(12) United States Patent
Goerne

(10) Patent No.: US 8,697,669 B2
(45) Date of Patent: Apr. 15, 2014

(54) FOLIC ACID-, VITAMIN B6- AND VITAMIN B12-CONTAINING AGENTS AND THE USE THEREOF

(75) Inventor: Martin Goerne, Hamburg (DE)

(73) Assignee: Phrontier S.A.R.L., Caudebec-en-Caux (FR)

( * ) Notice: Subject to any disclaimer, the term of this patent is extended or adjusted under 35 U.S.C. 154(b) by 792 days.

(21) Appl. No.: 11/817,713

(22) PCT Filed: Mar. 1, 2006

(86) PCT No.: PCT/EP2006/001875
§ 371 (c)(1),
(2), (4) Date: Sep. 24, 2008

(87) PCT Pub. No.: WO2006/092294
PCT Pub. Date: Sep. 8, 2006

(65) Prior Publication Data
US 2009/0054371 A1    Feb. 26, 2009

(30) Foreign Application Priority Data

Mar. 1, 2005    (DE) .................. 10 2005 009 379

(51) Int. Cl.
*A01N 43/04*  (2006.01)
*A61K 31/70*  (2006.01)
*A01N 43/40*  (2006.01)
*A61K 31/435* (2006.01)
*A61K 31/44*  (2006.01)

(52) U.S. Cl.
USPC ........................ 514/52; 514/277; 514/351

(58) Field of Classification Search
None
See application file for complete search history.

(56) References Cited

U.S. PATENT DOCUMENTS

| | | | |
|---|---|---|---|
| 5,563,126 A * | 10/1996 | Allen et al. | ............... 514/52 |
| 5,932,624 A | 8/1999 | Herbert | |
| 6,129,918 A | 10/2000 | Amagase | |
| 6,207,651 B1 | 3/2001 | Allen et al. | |
| 6,210,686 B1 * | 4/2001 | Bell et al. | ............... 424/400 |
| 6,274,170 B1 | 8/2001 | Heibel et al. | |
| 6,297,224 B1 | 10/2001 | Allen et al. | |
| 6,299,896 B1 | 10/2001 | Cooper et al. | |
| 7,994,142 B2 * | 8/2011 | Goerne | ............... 514/43 |
| 2003/0225030 A1 | 12/2003 | Allen et al. | |
| 2005/0032740 A1 * | 2/2005 | Venkataraman | ............... 514/52 |
| 2005/0222079 A1 | 10/2005 | Goerne | |

FOREIGN PATENT DOCUMENTS

| | | |
|---|---|---|
| CA | 2 476 017 | 8/2003 |
| EP | 0 595 005 A1 | 5/1994 |
| WO | WO 94/06415 | 3/1994 |
| WO | WO 03/068231 A2 | 8/2003 |

OTHER PUBLICATIONS (R) Naurath et al.(I), "Effects of Vitamin B12, Folate, and Vitamin B6 Supplements in Elderly People with Normal Serum Vitamin Concentrations," The Lancet, 346, 85-89 (Jul. 8, 1995).*
(S) Naurath et al.(II), "Does a Single Vitamin B-Supplementation Induce Functional Vitamin B-Deficiency?" Clinical Chemistry and Laboratory Medicine, 39(8), 768-771 (2001).*
(T) Beers et al. (eds.), Chapter 202 in The Merck Manual of Diagnosis and Therapy, 17th Edition, Merck & Co., Inc., Rahway, NJ, Jan. 1999, only text pp. 1658-1659 have been supplied by applicant.*
U.S. Appl. No. 11/813,729, filed Jul. 11, 2007, Goerne.

* cited by examiner

*Primary Examiner* — Lawrence E Crane
(74) *Attorney, Agent, or Firm* — Oblon, Spivak, McClelland, Maier & Neustadt, L.L.P.

(57) ABSTRACT

The invention relates to agents containing a folic acid, vitamin B6 and vitamin B12 and to the use thereof in hyperhomocystenemia for controlling homocysteine levels. The inventive agents are particularly suitable for preventive and acute treatment of vascular diseases of pregnant women and neurodegenerative diseases and are particularly advantageous in cases of hyperhomocysteinemia whose treatment with homocysteine level reducing agents causes secondary effects. Pharmaceutical agents and food supplements comprising the corresponding active substance combination, agents in the form of commercial packages containing corresponding combination preparations or monopreparations for a combined application are, in particular, also disclosed.

9 Claims, No Drawings

FOLIC ACID-, VITAMIN B6- AND VITAMIN B12-CONTAINING AGENTS AND THE USE THEREOF

CROSS-REFERENCE TO RELATED APPLICATIONS

This application is a 371 application of PCT/EP2006/001875 filed Mar. 1, 2006 and claims the benefit of DE 102005009379.5 filed Mar. 1, 2005.

The present invention relates to compositions comprising folic acid, vitamin B6 and vitamin B12, and to the use thereof for regulating homocysteine levels. The compositions can thus be used in particular for the preventive and acute treatment of vascular disorders. Descriptions are given in particular of pharmaceutical compositions and food supplements with a corresponding active ingredient combination, and compositions in the form of commercial packs with corresponding combination products or single-ingredient products for combined use.

It has recently been disclosed that homocysteine is a risk factor for coronary, peripheral and cerebral vascular disorders. Patients with hereditary hyperhomocysteinemia, an autosomal recessive disorder, have homocysteine plasma levels which are about 10-20 times higher than the normal levels. In children affected by the homozygous form of the disorder, vascular lesions become evident at an early date and represent the main cause of the frequently fatal outcome of the disorder in childhood. Whereas elevated homocysteine levels in the genetically related forms of hyperhomocysteinemia are usually attributable to a deficiency of cystathionine β-synthase and/or a mutation in 5,10-methylenetetrahydrofolate reductase, it is also possible for alterations in folic acid, vitamin B6, vitamin B12 and betaine metabolism to lead to elevated homocysteine levels. Accordingly, acquired types of hyperhomocysteinemia may also occur. For example, renal failure or a deficiency of folic acid, cobalamin and/or pyridoxine or metabolites thereof may lead to elevated homocysteine levels. Especially in elderly people, such a vitamin deficiency, which may be caused by an inadequate intake or by malabsorption, is regarded as the most frequent cause of acquired hyperhomocysteinemia.

Vitamin B12 is necessary in order to transfer a 1-carbon unit on folic acid to homocysteine and to convert the latter into methionine. Vitamin B6 is involved in a further metabolic pathway for the degradation of excess homocysteine.

It has already been proposed to employ a wide variety of folic acid, vitamin B6 and vitamin B12 containing vitamin products to reduce elevated homocysteine levels.

For example, U.S. Pat. No. 5,932,624 describes a composition which contains 500 μg of folic acid, 25 μg of vitamin B12 and 10 mg of vitamin B6. Depending on the patient's condition, in general 300 to 2000 μg of folic acid, 25 to 1000 μg of vitamin B12 and 5 to 20 mg of vitamin B6 should be administered for the homocysteine plasma levels to fall to normal levels.

The combination indicated in U.S. Pat. No. 6,274,170 of vitamins and aspirin for the treatment of atherosclerotic cardiovascular disorders contains 400 to 1000 μg of folic acid, 3 to 25 mg of vitamin B6 and 5 to 500 μg of vitamin B12.

A multivitamin and mineral supplement which, besides a number of other vitamins and essential trace elements, contains 800 μg of folic acid, 25 mg of vitamin B6 and 400 μg of vitamin B12 is described in U.S. Pat. No. 6,299,896. This composition is also said to be able to reduce the homocysteine levels.

Daily intake of 180 to 800 μg of folic acid, 1.6 to 4.6 mg of vitamin B6 and 1.5 to 4.0 μg of vitamin B12 together with β-glucan- or glucomannan-containing fibers is recommended in U.S. Pat. No. 6,210,686 in order to improve the composition of serum lipids, to reduce homocysteine levels and to protect lipoproteins from oxidation.

According to U.S. Pat. No. 6,297,224, and U.S. Pat. No. 6,207,651 and U.S. Pat. No. 5,563,126 which are related thereto, vitamin preparations which contain 0.4 mg or 1.0 mg of folic acid together with 25 mg of vitamin B6 and 2.0 mg of vitamin B12 are to be employed for the prevention and treatment of elevated homocysteine, cystathionine, methylmalonic acid or 2-methylcitric acid serum levels.

U.S. Pat. No. 6,129,918 describes a garlic-based composition for reducing homocysteine plasma levels. In addition to garlic or garlic extract, this composition may comprise folic acid, vitamin B6 and vitamin B12. The last three active ingredients mentioned are in this case intended to enhance the advantageous properties of garlic.

WO 03/068231 relates to compositions which comprise folic acid, vitamin B6 and vitamin B12, and to the use thereof for regulating homocysteine levels. The quantitative ratio of folic acid to vitamin B6 and of vitamin B12 to vitamin B6 is stated to be in a range from about 1:67 to 1:150 by weight, and the quantitative ratio of folic acid to vitamin B12 is stated to be in a range from about 1:0.67 to 1:1.50 by weight. These compositions have a reliable effect lowering homocysteine levels. It has, however, been found that unwanted side effects such as paresthesias on the extremities occurred in some patients treated in this way.

It has now surprisingly been found that such side effects can be avoided and homocysteine levels nevertheless effectively lowered on use of a combination reduced in the amount of vitamin B6 instead of the combination of folic acid, vitamin B6 and vitamin B12 disclosed in WO 03/068231.

The present invention therefore relates to compositions based on folic acid, vitamin B6 and vitamin B12 or physiologically acceptable derivatives and/or salts thereof, characterized in that the quantitative ratio of folic acid to vitamin B6 and of vitamin B12 to vitamin B6 is in a range from about 1:33 to about 1:75, and the quantitative ratio of folic acid to vitamin B12 is in a range from about 1:0.67 to about 1:1.50.

The inventive compositions based on folic acid, physiologically acceptable derivatives or salts thereof (also referred to for simplicity as "folic acids" or "folic acid component"), vitamin B6, physiologically acceptable derivatives or salts thereof (also referred to for simplicity as "B6 vitamins" or "vitamin B6 component") and vitamin B12, physiologically acceptable derivatives or salts thereof (also referred to for simplicity as "B12 vitamins" or "vitamin B12 component") offer considerable advantages in regulating homocysteine levels and thus in the preventive and acute treatment of vascular disorders.

The present invention therefore also relates to the use of the inventive combination of folic acid, vitamin B6 and vitamin B12 or physiologically acceptable derivatives and/or salts thereof for regulating the homocysteine level. The regulation relates in particular in the acute sphere to the reduction of elevated homocysteine levels, i.e. in particular the treatment of hyperhomocysteinemia, and in the prophylactic sphere to the prevention of elevated homocysteine levels and the maintenance of normal homocysteine levels. The regulation of homocysteine levels is associated in particular with a prophylactic treatment of disorders connected with elevated homocysteine levels, i.e. especially those accompanied or caused by elevated homocysteine levels.

The present invention therefore further relates to the use of the inventive combination of folic acid, vitamin B6 and vitamin B12 or physiologically acceptable derivatives and/or salts thereof for treating disorders which are connected with an elevated homocysteine level. These include in particular vascular disorders such as arteriosclerosis, venous thromboses and arterial occlusions, fetal damage such as neural tube defects, and neurodegenerative disorders such as certain types of Alzheimer's dementia.

In this sense, the invention also relates to compositions for regulating the homocysteine level and for treating disorders which are connected with elevated homocysteine levels. These compositions are based on the inventive active ingredient combination and, where appropriate, further active ingredients, it being preferable for the active ingredients or active ingredient components to be formulated together in one formulation or separately in at least two or three different formulations.

Particular advantages of a use of the active ingredient combination of the invention emerge in certain patient groups in which treatment with compositions lowering homocysteine levels is associated with side effects. These include in particular paresthesias in the region of the extremities, in particular on the hand, arm, foot and/or leg, which appear to be connected with administration of a relatively large amount of vitamin B6. It is therefore preferred according to the invention to limit the quantitative ratio of folic acid and/or vitamin B12 to vitamin B6 to not more than 1:66 (i.e. the amount of vitamin B6 is not more 66 times the amount of folic acid or vitamin B12). This applies particularly when the daily dose of folic acid and vitamin B12 is chosen in each case to be relatively high at up to 1.2 mg. A further possibility, independent thereof, is to limit the maximum daily dose of vitamin B6 to less than 70 mg.

Preferred compositions and uses are those in which the quantitative ratio of folic acid to vitamin B6 is in a range from about 1:33 to about 1:66, the quantitative ratio of vitamin B12 to vitamin B6 is in a range from about 1:33 to about 1:66, and the quantitative ratio of folic acid to vitamin B12 is in a range from about 1:0.67 to about 1:1.50.

Advantageous compositions and uses are those in which the quantitative ratio of folic acid to vitamin B6 is in a range from about 1:41 to about 1:61, the quantitative ratio of vitamin B12 to vitamin B6 is in a range from about 1:41 to about 1:61, and the quantitative ratio of folic acid to vitamin B12 is in a range from about 1:0.82 to about 1:1.22.

Particularly advantageous compositions and uses are those in which the quantitative ratio of folic acid to vitamin B6 to vitamin B12 is about 1 to 50 to 1.

According to a particular aspect of the invention, the active ingredients are used in the quantitative ratios indicated above in such a way that preferably a daily dose of less than 70 mg of vitamin B6, in particular of less than 65 mg of vitamin B6 and especially of not more than 60 mg of vitamin B6 is administered to an individual to be treated and having the average adult weight of about 75 kg.

In this connection, the stated quantitative ratios relate to quantities by weight of the active ingredients folic acid, vitamin B6 and vitamin B12, so that an appropriate conversion must take place where necessary for salts and derivatives. This applies analogously to the active ingredient contents indicated in the present description. Alternatively, the ratios can also be based on molar quantities, so that on the assumption that one mole of the relevant derivative or salt comprises one mole of folic acid, vitamin B6 or vitamin B12, the molar quantitative ratios for folic acid, vitamin B6, vitamin B12 and their derivatives and/or salts can be expressed uniformly.

"Folic acid" refers according to the invention to N-pteroyl-glutamic acid of the formula I

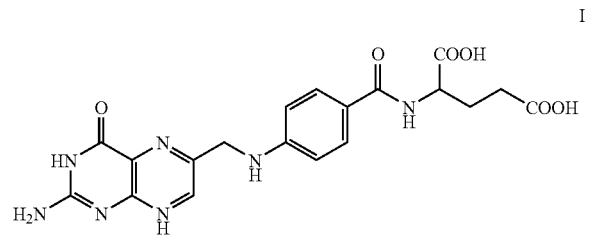 [SMILES: Nc1nc2ncc(CNc3ccc(C(=O)NC(CCC(=O)O)C(=O)O)cc3)nc2c(=O)[nH]1]

I including the optical isomers covered by this formula, both as mixtures, e.g. as racemate, and in pure form, e.g. R or S enantiomers. N-Pteroyl-L-glutamic acid of the formula Ia

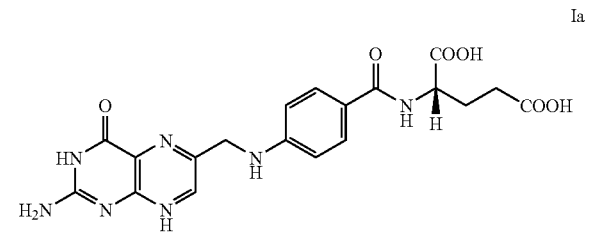 [SMILES: Nc1nc2ncc(CNc3ccc(C(=O)N[C@@H](CCC(=O)O)C(=O)O)cc3)nc2c(=O)[nH]1]

Ia is preferred. The folic acid derivatives include in particular folic acid metabolites, amides and esters of folic acid, as well as the metabolites. Amides and esters which can be hydrolyzed under physiological conditions, such as amides with $C_1$-$C_{10}$-alkylamines or esters with $C_1$-$C_{10}$-alcohols are advantageous. A particular form of the amides are N-pteroylpolyglutamic acids.

The folic acid metabolites include in particular $H_4$-folic acids of the formula Ib

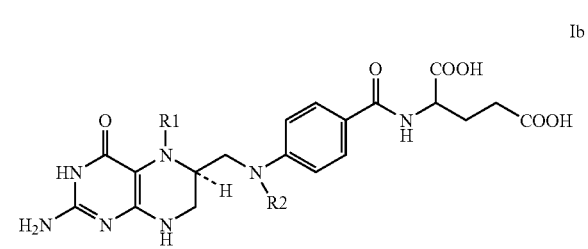

Ib in which R1 is hydrogen, methyl, —HC=O (formyl) or —HC=NH (formimino), and R2 is hydrogen or —HC=O (formyl), or R1 and R2 together form a methylene or methenyl bridge. The optical isomers covered by this formula are included in accordance with the above statements, with preference for the L-glutamic acid derivatives in this case too. Particular mention should be made of tetrahydrofolic acid, 5-methyltetrahydrofolic acid, 5,10-methylenetetrahydrofolic acid, 5-formyltetrahydrofolic acid, 10-formyltetrahydrofolic acid, 5-formiminotetrahydrofolic acid and 5,10-methenyltetrahydrofolic acid.

The physiologically acceptable salts of folic acid and folic acid derivatives include acid and base addition salts and appropriate mixed forms.

The acid addition salts include salts of folic acid or folic acid derivatives with inorganic acids such as hydrochloric acid, sulfuric acid, nitric acid or phosphoric acid, or organic acids, in particular carboxylic acids, e.g. acetic acid, tartaric acid, lactic acid, citric acid, malic acid, mandelic acid, ascorbic acid, maleic acid, fumaric acid, gluconic acid or sulfonic acids, e.g. methanesulfonic acid, benzenesulfonic acid and toluenesulfonic acid, and the like.

The base addition salts include salts of folic acid or folic acid derivatives with inorganic bases, for example metal hydroxides or carbonates of alkali metals, alkaline earth metals or transition metals, or with organic bases, for example ammonia or basic amino acids such as arginine and lysine, amines, e.g. methylamine, dimethylamine, trimethylamine, triethylamine, ethylamine, diethylamine, ethylene-diamine, ethanolamine, diethanolamine, 1-amino-2-propanol, 3-amino-1-propanol or hexamethylenetetramine, saturated cyclic amines having 4 to 6 ring carbon atoms, such as piperidine, piperazine, pyrrolidine and morpholine, and further organic bases, for example N-methylglucamine, creatine and tromethamine, and quaternary ammonium compounds such as tetramethylammonium and the like.

Salts with inorganic bases are preferred, e.g. Na, K, Mg, Ca, Zn, Cr and Fe folates.

"Vitamin B6" designates according to the invention 4,5-bis(hydroxymethyl)-2-methyl-3-pyridinol of the formula II

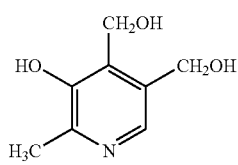

II also referred to as pyridoxine (INN).

The vitamin B6 derivatives include in particular pyridoxals and pyridoxamines, and esters of pyridoxines, pyridoxals and pyridoxamines. Also advantageous in this case are esters which can be hydrolyzed under physiological conditions.

Particular mention should be made in this connection of the pyridoxines, pyridoxals and pyridoxamines of the formula IIa

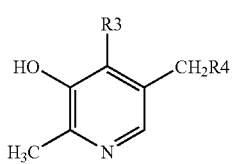

IIa in which $R_3$ is $CH_2OH$, CHO or $CH_2NH_2$, and $R^4$ is OH or $OPO_3H_2$.

Physiologically acceptable salts of vitamin B6 or vitamin B6 derivatives include in particular acid addition salts, e.g. with the abovementioned inorganic and organic acids. Particular mention should be made of the hydrochloride, especially pyridoxine HCl.

"Vitamin B12" is also referred to as cyanocobalamin or cobalamin.

Vitamin B12 derivatives include in particular cobalamins in which the cyano group of the cyanocobalamin is replaced by other cobalt coordination partners. These include in particular hydroxocobalamin, aquocobalamin, nitrosocobalamin, methylcobalamin and adenosylcobalamin (coenzyme B12).

Physiologically acceptable salts of vitamin B12 or vitamin B12 derivatives include in particular acid addition salts, e.g. with the abovementioned inorganic and organic acids. The acetate of hydroxocobalamin should be mentioned in particular.

Folic acids, B6 and B12 vitamins are sufficiently well known and can be either purchased or made available in a manner known per se.

Besides the folic acid, vitamin B6 and vitamin B12 components, the inventive compositions may include further active ingredients. These active ingredients may be in particular those whose effect is similar to the effect mediated by folic acid, vitamin B6 and vitamin B12 or supplements the latter and which in particular complies with the inventive purposes of use. Thus, in addition to the inventive combination, it may be advantageous to administer active ingredients which lower the homocysteine level, antithrombotics, antisclerotics and the like.

Assays for determining homocysteine levels, which are normally in the range from 5 to 15 µmol/l of blood plasma, are known (cf. for example the prior art described at the outset). Elevated homocysteine levels are referred to as hyperhomocysteinemia. Elevated homocysteine levels can be reduced or preventively averted with the aid of the inventive compositions.

Depending on the homocysteine level, hyper-homocysteinemias are divided into three classes:

Mild hyperhomocysteinemias are characterized by homocysteine levels in a range from more than 15 and up to 30 µmol/l of blood plasma.

Moderate hyperhomocysteinemias are characterized by homocysteine levels in the range from more than 30 and up to 100 µmol/l of blood plasma.

High hyperhomocysteinemias are characterized by homocysteine levels of more than 100 µmol/l of blood plasma.

Particular advantages emerge according to the invention in relation to the treatment of moderate hyperhomocysteinemias.

The present invention is directed in particular to the treatment of one or more of the following pathological states:

Hereditary hyperhomocysteinemia. The pathological state of hereditary hyperhomocysteinemia is characterized by genetically related disturbances of homocysteine metabolism. Metabolic disturbances of this type include in particular an absence (homozygous form) or deficiency (heterozygous form) of cystathionine β-synthase, a deficiency of methylenetetrahydrofolate reductase, a mutation-related modification of methylenetetrahydrofolate reductase into a thermolabile derivative thereof, and a number of other alterations in folic acid, vitamin B6, vitamin B12 and betaine metabolism. The signs and symptoms of hereditary hyperhomocysteinemia include homocysteinuria, mental retardation, dislocation of the lens of the eye, skeletal abnormalities and/or vascular disorders, which can thus be treated acutely or preventively according to the invention as symptom or syndrome.

Acquired hyperhomocysteinemia. Acquired types of hyperhomocysteinemia are usually characterized by manifestations of deficiency which lead to accumulation of homocysteine. For example, deficiencies of folic acid and folic acid derivatives, vitamin B12 and vitamin B12 derivatives, vitamin B6 and vitamin B6 derivatives, and a general vitamin deficiency, may lead to elevated homocysteine levels. It is moreover possible for the vitamin deficiency to be caused for example by an inadequate intake or by malabsorption of the respective vitamin(s). Elevated homocysteine levels may also be caused by medicaments able to influence folic acid metabolism, such as methotrexate or anticonvulsants; able to influence vitamin B12 metabolism, such as nitrates; or able to influence vitamin B6 metabolism, such as theophylline. In addition, the homocysteine plasma level is influenced by age, gender, cigarette smoking, essential hypertension, hypercholesterolemia and insufficient exercise.

The present invention is additionally directed at the treatment of disorders which are connected with elevated homocysteine levels, in particular are associated therewith or caused thereby. These include in particular vascular disorders, fetal malformations and certain neurodegenerative disorders. Prevention is particularly important in this area of indications.

Vascular disorders means disorders of the peripheral, coronary and cerebral vessels. Particular mention should be made of alterations in vascular endothelial cells, proliferation of muscle cells and/or thickening of the intima of vessels. It is thus possible to treat according to the invention in particular arterioscleroses, venous thromboses, arterial occlusions and further arteriovenous vascular disorders.

Fetal malformations, especially neural tube defects, may occur if the mother suffers from elevated homocysteine levels during pregnancy.

Elevated homocysteine levels may also be involved in neurodegenerative disorders, especially vascular forms of dementia in the elderly.

The invention is thus directed according to a particular aspect at reducing the risk of the occurrence of the vascular disorders, fetal malformations and neurodegenerative disorders described above.

Particular advantages of a use of the active ingredient combination of the invention emerge in certain patient groups in which administration of folic acid, vitamin B6 and vitamin B12 to lower the homocysteine level may induce side effects. These include in particular patients in whom paresthesias occur in the region of the extremities, in particular on the hand, arm, foot and/or leg. Such side effects appear to occur more often in particular when the daily dose of vitamin B6 is more than 70 mg, 80 mg, 90 mg, or even 100 mg.

The inventive compositions and uses become increasingly important in adults with increasing age. The treatment has particular advantages in the group of over 40s and especially the over 50s. The inventive treatment is indicated in particular when there is evidence of arterioscleroses, arterial occlusions, venous thromboses and/or vascular forms of dementia in the elderly, or there is a risk of these disorders. A further group in which the inventive treatment may have particular advantages are children with hereditary hyperhomocysteinemia, and pregnant women, even if there is no evidence of vascular disorders and the homocysteine levels are only slightly elevated.

According to the invention, the individual to be treated, preferably a mammal, especially a human and also a productive or domestic animal, receives administration of an effective amount of the inventive active ingredient combination of folic acid component, vitamin B6 component and vitamin B12 component, usually formulated in accordance with pharmaceutical, veterinary or food technological practice. An amount is effective according to the invention especially when it brings about a significant reduction in the homocysteine level, advantageously into the normal range.

The treatment usually takes place by single or multiple daily administration of a suitable dose, where appropriate together or alternately with other active ingredients or active ingredient-containing products, so that an individual to be treated with the weight of an average adult of about 75 kg usually receives administration of a minimum daily dose of about 0.8 mg, preferably about 0.9 mg and advantageously about 1 mg, of folic acid; of about 40 mg, preferably about 45 mg and advantageously about 50 mg, of vitamin B6; and of about 0.8 mg, preferably about 0.9 mg and advantageously about 1 mg, of vitamin B12. According to another aspect, the maximum daily dose is usually about 1.2 mg, preferably about 1.1 mg and advantageously about 1 mg, of folic acid; about 60 mg, preferably about 55 mg and advantageously about 50 mg, of vitamin B6; and about 1.2 mg, preferably about 1.1 mg and advantageously about 1 mg, of vitamin B12. The daily dose should be adjusted appropriately if the weight differs from the average. This adjustment takes place in a conventional way by the skilled worker, if necessary taking account of analytical investigations. In addition, differences in the daily dose prescribed by the physician may also arise owing to the state of health of the individual to be treated.

The treatment usually takes place over an appropriate period in the region of days or weeks. It is expedient to normalize the homocysteine levels within a treatment period of about 1 to 4 weeks. If necessary, the treatment is also continued after the homocysteine levels have normalized. This applies in particular to the hereditary types of hyperhomocysteinemia and acquired types in which a causative treatment is not possible or has no success, and discontinuation of the inventive treatment would result in a renewed rise in the homocysteine levels.

The invention also relates to the production of compositions for the treatment of an individual, preferably a mammal, in particular a human and also a productive or domestic animal.

The compositions include in particular pharmaceutical compositions, food supplements and food products, e.g. functional or dietetic food products. The inventive food products have, besides a function predominantly related to nutritional value, additionally a function related to the active ingredients and particularly related to the inventive active ingredient combination. They are therefore referred to as functional or dietetic food or nutritional products. Food supplements serve to supplement the daily diet with the inventive active ingredient combination, in which case the function related to the nutritional value of the food supplement becomes less important as such.

According to one aspect, the present invention relates to formulations comprising
i) at least one active ingredient from the folic acid group (folic acid, physiologically acceptable derivatives and/or salts thereof),
ii) at least one active ingredient from the vitamin B6 group (vitamin B6, physiologically acceptable derivatives and/or salts thereof), and
iii) at least one active ingredient from the vitamin B12 group (vitamin B12, physiologically acceptable derivatives and/or salts thereof), and
where appropriate at least one further active ingredient and a formulation base, in the quantitative ratios indicated according to the invention.

Thus, the active ingredient combination comprises for the purposes of the invention as active ingredient component i) folic acid, a physiologically acceptable derivative and/or salt thereof. Mixtures of these forms are possible but are to be considered only in particular cases. According to a particular embodiment, active ingredient component i) consists of at least 90% by weight folic acid.

The active ingredient combination additionally comprises for the purposes of the invention as active ingredient component ii) vitamin B6, a physiologically acceptable derivative and/or salt thereof. Mixtures of these forms are likewise possible, but are to be considered only in particular cases.

According to a particular embodiment, active ingredient component ii) consists of at least 90% by weight pyridoxine HCl.

The active ingredient combination additionally comprises for the purposes of the invention as active ingredient component iii) vitamin B12, a physiologically acceptable derivative and/or salt thereof. Mixtures of these forms are likewise possible, but are to be considered only in particular cases. According to a particular embodiment, active ingredient component iii) consists of at least 90% by weight cobalamin.

The content of the active ingredient combination in the formulation is larger than the content present where appropriate in natural sources, in particular food products. In this sense, the inventive compositions are fortified in relation to the active ingredient combination. The content of active ingredient combination of i), ii) and iii) in the formulation is preferably at least about 0.01% by weight, advantageously at least about 0.05% by weight and in particular at least about 0.1% by weight. In the case of a pharmaceutical composition, the content is usually about 1 to 60% by weight, preferably about 5 to 35% by weight, and in particular about 10 to 30% by weight, and in the case of a food supplement and especially in the case of food products where appropriate correspondingly lower if the formulation is given in larger amounts. The formulations preferably comprise the indicated daily dose.

Unless otherwise indicated, data in % by weight are based on the total weight of the formulation.

The formulation base for novel formulations comprises physiologically acceptable excipients. Physiologically acceptable excipients are those known to be usable in the sectors of pharmacy, food technology and adjacent areas, in particular the excipients listed in relevant pharmacopeias (e.g. DAB, Ph. Eur., BP, NF), and other excipients whose properties do not stand in the way of physiological use. Excipients for the purposes of the invention may also have a nutritional value and are therefore generally used as food component. They may also include nutrients, especially essential nutrients.

Suitable excipients may be: wetting agents; emulsifying and suspending agents; preservatives; antioxidants; antiirritants; chelating agents; tablet coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients such as binders, fillers, lubricants, disintegrants or coatings; propellants; desiccants; opacifiers; thickeners; waxes; plasticizers; white oils. An arrangement concerning this is based on specialist knowledge as described, for example, in Fiedler, H. P., Lexikon der Hilfsstoffe für Pharmazie, Kosmetik und angrenzende Gebiete, 4th edition, Aulendorf: ECV-Editio-Cantor-Verlag, 1996.

Food components usually comprise one or more amino acids, carbohydrates or fats and are suitable for the human and/or animal diet. They comprise individual components, frequently vegetable but also animal products, especially sugars, where appropriate in the form of syrups, fruit preparations such as fruit juices, nectar, fruit pulps, purees or dried fruit, for example apple juice, grapefruit juice, orange juice, apple purée, tomato sauce, tomato juice, tomato purée; cereal products such as wheat flour, rye flour, oat flour, corn flour, barley flour, spelt flour, corn syrup and starches from said cereals; dairy products such as milk protein, whey, yoghurt, lecithin and lactose.

Essential nutrients include, in particular, vitamins, provitamins, trace elements, amino acids and fatty acids. Essential amino acids which may be mentioned are isoleucine, leucine, lysine, methionine, phenylalanine, threonine, tryptophan and valine. They also include semiessential amino acids which must be given, for example, in periods of growth or deficiency states, such as arginine, histidine, cysteine and tyrosine. Trace elements which may be mentioned are: essential trace elements which have been proved to be necessary for humans and deficiency of which leads to manifestation of signs and symptoms: iron, copper, zinc, chromium, selenium, calcium, magnesium, potassium, lithium, cobalt, molybdenum, iodine, silicon, fluorine, manganese. Likewise elements whose function in humans is as yet inadequately verified: tin, nickel, vanadium, arsenic, manganese. Fatty acids essential for humans which may be mentioned are: linoleic acid and linolenic acid. A comprehensive list of vitamins is to be found in "Referenzwerte für die Nährstoffzufuhr", 1st edition, Umschau Braus Verlag, Frankfurt am Main, 2000, edited by the Deutsche Gesellschaft für Ernährung.

The total of active ingredient component and formulation base is usually 100% by weight.

Examples of suitable formulations for food supplementation are capsules, tablets, pills, powder sachets, liquid ampoules and bottles with stopper inserts, besides the drug forms mentioned below.

Examples of suitable pharmaceutical formulations are solid drug forms such as oral powders, dusting powders, granules, tablets, especially film-coated tablets, pastilles, sachets, cachets, sugar-coated tablets, capsules such as hard and soft gelatin capsules, suppositories or vaginal drug forms, semisolid drug forms such as ointments, creams, hydrogels, pastes or patches, and liquid drug forms such as solutions, emulsions, especially oil-in-water emulsions, suspensions, for example lotions, preparations for injection and infusion, eye drops and ear drops. It is also possible to use implanted delivery devices for administering active ingredients of the invention. Liposomes or microspheres may also be used.

Food formulations usually have the customary form and are preferably made available in the form of infant food, breakfast products, especially in the form of mueslis or bars, sports beverages, complete meals, especially in the framework of complete balanced diets, dietetic products such as diet drinks, diet meals and diet bars.

The formulations are preferably administered by the oral route, but they can also be administered, especially in the pharmaceutical sector, by the rectal, transdermal, subcutaneous, intravenous, intramuscular or intranasal route.

For producing the compositions, the active ingredients are usually mixed or diluted with a suitable excipient. Excipients may be solid, semisolid or liquid materials serving as vehicle, carrier or medium for the active ingredient. Admixture of other excipients takes place, if necessary, in a manner known per se. It is possible to carry out shaping steps, where appropriate in conjunction with mixing processes, e.g. a granulation, compression and the like.

The active ingredient components can in particular be formulated together. However, they also be initially processed separately and subsequently combined in a compartmented, e.g. multilayer pharmaceutical form. It is thus possible to take account of possible active ingredient incompatibilities and different active ingredient properties such as bioavailability, stability, solubility and the like.

The present invention is explained in more detail by means of the following examples without being restricted thereto.

EXAMPLE 1

Pharmaceutical Compositions

| a) Soft gelatin capsules (folic acid 1 mg + vitamin B6 50 mg + vitamin B12 1 mg) | |
|---|---|
| Filling: | |
| folic acid | 1 mg |
| vitamin B6 | 50 mg |
| vitamin B12 | 1 mg |
| soybean oil (refined) | 440 mg |
| soybean lecithin (E322) | 50 mg |
| colloidal silica | 5 mg |
| Capsule shell: | |
| gelatin | 303 mg |
| glycerol 85% | 87 mg |
| sorbitol 70% | 77 mg |
| purified water | 52 mg |
| iron oxide pigment brown 75 (E 172) | 3 mg |
| b) Tablet (folic acid 1 mg + vitamin B6 50 mg + vitamin B12 1 mg) | |
| folic acid | 1 mg |
| vitamin B6 | 50 mg |
| vitamin B12 | 1 mg |
| lactose | 127.5 mg |
| magnesium stearate | 5 mg |
| talc | 23.75 mg |
| microcrystalline cellulose | 81 mg |

EXAMPLE 2

Patient after Myocardial Infarction

The homocysteine level of a 42-year old man after myocardial infarction was 39.3 μmol/l. On daily oral administration of 1 mg of folic acid, 1 mg of vitamin B12 and 100 mg of vitamin B6 to this man, the homocysteine level fell to 12.1 μmol/l after 8 weeks. No further reduction occurred during the subsequent 3 months, despite continuation of the therapy. On discontinuation of the therapy, the homocysteine level again rose to 39.3 μmol/l within 8 weeks.

On daily oral administration now of 1 mg of folic acid, 1 mg of vitamin B12 and 50 mg of vitamin B6, the homocysteine level fell to 14.6 μmol/l after therapy for 8 weeks.

Further attempts at therapy with different quantitative ratios of the three active ingredients led to a comparatively smaller lowering of the homocysteine level. Thus, the homocysteine level fell only to 34.5 μmol/l on daily oral administration of 1 mg of folic acid, 1 mg of vitamin B12 and 75 mg of vitamin B6.

EXAMPLE 3

Patient with Insulin-Dependent Diabetes Mellitus, Leg Ulcer Associated with Nicotine Abuse The homocysteine level of a 39-year old patient with insulin-dependent diabetes mellitus, leg ulcer associated with nicotine abuse was 49.1 μmol/l.

On daily oral administration of 1 mg of folic acid, 1 mg of vitamin B12 and 100 mg of vitamin B6 to this man, the homocysteine level fell to 16.3 μmol/l. However, even on day 8 after the start of therapy there was repeated tingling on the hands, arms and legs of the patient. On discontinuation of the therapy, the homocysteine level rose to 49.2 μmol/l again after 4 weeks.

Subsequent therapy with daily oral administration of 1 mg of folic acid, 1 mg of vitamin B12 and 50 mg of vitamin B6 led to a reduction in the homocysteine level to 18.2 μmol/l after 8 weeks. The side effects observed previously did not occur in this case.

On discontinuation of this therapy, the homocysteine level again rose to 49.2 μmol/l after 8 weeks.

The invention claimed is:

1. A composition based on folic acid, vitamin $B_6$ and vitamin $B_{12}$ or physiologically acceptable derivatives and/or salts thereof, wherein the quantitative folic acid:vitamin $B_6$ and vitamin $B_{12}$:vitamin $B_6$ ratios are in a range of 1:33-66 by weight, and the quantitative folic acid:vitamin $B_{12}$ ratio is in a range of 1:0.67-1.50 by weight and when administered as a single daily dosage form or multiple daily dosage form, a daily dose amount from 0.8 mg to 1.2 mg of folic acid, from 40 mg to 60 mg of vitamin $B_6$ and from 0.8 mg to 1.2 mg of vitamin $B_{12}$, wherein the physiologically acceptable derivatives are a compound of formula IIa

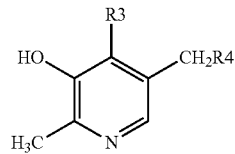

wherein R3 is CHO and R4 is OH or a physiologically acceptable salt thereof, a compound of formula IIa wherein R3 is $CH_2NH_2$ and R4 is OH or a physiologically acceptable salt thereof, hydroxocobalamine or a physiologically acceptable salt thereof, methylcobalamine or a physiologically acceptable salt thereof, or adenosylcobalamine, or a physiologically acceptable salt thereof.

2. The composition as claimed in claim 1, wherein the quantitative folic acid:vitamin $B_6$ and vitamin $B_{12}$:vitamin $B_6$ ratios are in a range of 1:41-61 by weight, and the quantitative folic acid:vitamin $B_{12}$ ratio is in a range of 1:0.82-1.22 by weight.

3. The composition as claimed in claim 1, wherein the quantitative folic acid:vitamin $B_6$:vitamin $B_{12}$ ratio is about 1:50:1 by weight.

4. The composition as claimed in claim 1, where the effective amount is a daily dose from 0.9 mg to 1.1 mg of folic acid, from 45 mg to 55 mg of vitamin $B_6$ and from 0.9 mg to 1.1 mg of vitamin $B_{12}$.

5. The composition as claimed in claim 1, where the effective amount is a daily dose of 1 mg of folic acid, 50 mg of vitamin $B_6$ and 1 mg of vitamin $B_{12}$.

6. A method of regulating homocysteine levels which comprises administering an effective amount of folic acid, vitamin $B_6$ and vitamin $B_{12}$ or physiologically acceptable derivatives and/or salts thereof to a subject in need thereof, wherein the quantitative folic acid:vitamin $B_6$ and vitamin $B_{12}$:vitamin $B_6$ ratios are in a range of 1:33-75 by weight, and the quantitative folic acid:vitamin $B_{12}$ ratio is in a range of 1:0.67-1.50 by weight, the daily dose being less than 70 mg of vitamin $B_6$, wherein the effective amount administered as a single daily dosage form or multiple daily dosage form, a daily dose amount from 0.8 mg to 1.2 mg of folic acid, from 40 mg to 60 mg of vitamin $B_6$ and from 0.8 mg to 1.2 mg of vitamin $B_{12}$, wherein the physiologically acceptable derivatives are a compound of formula IIa

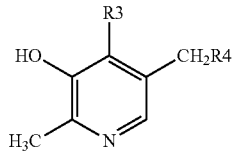

wherein R3 is CHO and R4 is OH or a physiologically acceptable salt thereof, a compound of formula IIa wherein R3 is $CH_2NH_2$ and R4 is OH or a physiologically acceptable salt thereof, hydroxocobalamine or a physiologically acceptable salt thereof, methylcobalamine or a physiologically acceptable salt thereof, or adenosylcobalamine, or a physiologically acceptable salt thereof.

7. The method as claimed in claim 6, where the effective amount is a daily dose from 0.9 mg to 1.1 mg of folic acid, from 45 mg to 55 mg of vitamin $B_6$ and from 0.9 mg to 1.1 mg of vitamin $B_{12}$.

8. The method as claimed in claim 6, where the effective amount is a daily dose of 1 mg of folic acid, 50 mg of vitamin $B_6$ and 1 mg of vitamin $B_{12}$.

9. The method as claimed in claim 6, comprising reducing elevated homocysteine residues in the subject, wherein the subject has hyperhomocysteinemia.

* * * * *